(12) United States Patent
Cheng et al.

(10) Patent No.: US 11,154,628 B2
(45) Date of Patent: Oct. 26, 2021

(54) SELF-STERILIZING SENSOR

(71) Applicant: International Business Machines Corporation, Armonk, NY (US)

(72) Inventors: Kangguo Cheng, Schenectady, NY (US); Shawn Peter Fetterolf, Cornwall, VT (US); Donald Francis Canaperi, Bridgewater, CT (US); Lawrence A. Clevenger, Saratoga Springs, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 178 days.

(21) Appl. No.: 16/107,231

(22) Filed: Aug. 21, 2018

(65) Prior Publication Data

US 2020/0061221 A1 Feb. 27, 2020

(51) Int. Cl.
*A61L 2/04* (2006.01)
*G06F 3/041* (2006.01)
*A61L 2/24* (2006.01)

(52) U.S. Cl.
CPC .................. *A61L 2/04* (2013.01); *A61L 2/24* (2013.01); *G06F 3/0416* (2013.01); *A61L 2202/14* (2013.01)

(58) Field of Classification Search
CPC .......... A61L 2/04; A61L 2/24; A61L 2202/14; G06F 3/0416; G06F 2203/04105
See application file for complete search history.

(56) References Cited

U.S. PATENT DOCUMENTS

| | | | |
|---|---|---|---|
| 4,677,280 A | 6/1987 | Kai | |
| 7,692,159 B2 | 4/2010 | Lane et al. | |
| 8,084,752 B2 | 12/2011 | Ranta et al. | |
| 8,114,346 B2 | 2/2012 | Hyde et al. | |
| 8,597,569 B2 | 12/2013 | Gruen et al. | |
| 9,623,138 B2 | 4/2017 | Pagan et al. | |
| 9,772,714 B2* | 9/2017 | Cohen | ........................ A61L 2/10 |
| 2008/0187190 A1* | 8/2008 | Shin | .................. G06K 9/00053 |
| | | | 382/124 |
| 2009/0048648 A1 | 2/2009 | Dacey et al. | |
| 2011/0286882 A1 | 11/2011 | Wu | |
| 2011/0291995 A1 | 12/2011 | Shr et al. | |

(Continued)

FOREIGN PATENT DOCUMENTS

| | | | |
|---|---|---|---|
| EP | 3043244 A1 | 7/2016 | |
| JP | 2006-75314 A | * 3/2006 | ............. A47K 13/30 |

OTHER PUBLICATIONS

Creative mechanisms, Everything you need to know about Polypropylene Plastic (Year: 2016).*

(Continued)

*Primary Examiner* — Sean E Conley
*Assistant Examiner* — Brendan A Hensel
(74) *Attorney, Agent, or Firm* — Amin, Turocy & Watson, LLP

(57) ABSTRACT

Techniques regarding self-sterilizing touch sensors are provided. For example, one or more embodiments described herein can comprise an apparatus, which can comprise a heating element. Also, the apparatus can comprise a protective layer adjacent to the heating element. The heating element can generate heat based on a pressure applied to the protective layer and can sterilize the protective layer.

17 Claims, 10 Drawing Sheets

(56) References Cited

U.S. PATENT DOCUMENTS

| | | | |
|---|---|---|---|
| 2015/0102024 A1* | 4/2015 | Barfuss | B60N 2/002 |
| | | | 219/204 |
| 2016/0000951 A1* | 1/2016 | Kreiner | A61L 2/10 |
| | | | 422/24 |
| 2016/0030612 A1 | 2/2016 | Kim et al. | |
| 2016/0158396 A1* | 6/2016 | Beckman | F24D 19/1051 |
| | | | 422/28 |
| 2019/0038792 A1* | 2/2019 | Kreiner | A61L 2/24 |

OTHER PUBLICATIONS

Translation of UNO (Year: 2006).*
Vivint.smarthome, How Wood Floors Can Save You Energy and Money (Year: 2015).*
Safet.BLR, Workplace Safety Reference Materials (Year: 2015).*
"The only FDA approved self-sanitizing keyboard and mouse." Stat Infomatic Solutions, 2 pages. https://www.statisllc.com/wp-content/uploads/Keyboard-Sell-Sheet-4.1.17.pdf. Last Accessed Aug. 8, 2018.
Uchida, Satoshi, et al. "Efficient sterilization of bacteria by pulse electric field in micro-gap." Journal of Electrostatics, vol. 66, Issues 7-8, Jul. 2008, pp. 427-431. 5 pages. https://www.sciencedirect.com/science/article/abs/pii/S030438860800051X.

* cited by examiner

SELF-STERILIZING SENSOR

BACKGROUND

The subject disclosure relates to a self-sterilizing sensor, and more specifically, to a touch sensor that can autonomously perform a self-sterilization based on a pressure applied to the touch sensor.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, apparatuses and/or methods regarding one or more self-sterilizing touch sensors are described.

According to an embodiment, an apparatus is provided. The apparatus can comprise a heating element. Also, the apparatus can comprise a protective layer adjacent to the heating element. The heating element can generate heat based on a pressure applied to the protective layer and can sterilize the protective layer.

According to an embodiment, an apparatus is provided. The apparatus can comprise a sterilization generator. Also, the apparatus can comprise a protective layer adjacent to the sterilization generator. The sterilization generator can sterilize the protective layer based on a pressure applied to the protective layer.

According to an embodiment, a method is provided. The method can comprise detecting, by a touch sensor, a pressure applied to a protective layer of the touch sensor. The method can also comprise sterilizing, by the touch sensor, the protective layer based on the detected pressure.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Touch sensors are widely used in a variety of applications, such as fingerprint sensors for identification purposes. For instance, the use of a touch sensor instead of software credentials to facilitate security measures has grown rapidly with interest in the Internet-of-things. However, use of the touch sensors can result in deposition of microbes on the surface of the touch sensors, which can potentially cause health issues. For example, the use of a touch sensor by various people can enable distribution of the one or more microbes to multiple individuals, and thereby exacerbate health concerns.

Various embodiments provided herein can comprise apparatuses and/or methods regarding one or more touch sensors with self-sterilization capabilities. In one or more embodiments, the touch sensors can comprise sterilization generators capable of initiating one or more sterilization processes to sterilize one or more surfaces of the touch sensor. Also, in one or more embodiments, the touch sensors can utilize sensing units comprised within the respective touch sensor to initiate the one or more sterilization processes. Further, the sterilization processes can comprise generating heat, electrical fields, and/or magnetic fields to sterilize one or more microbes. In addition, the one or more sterilization processes can be performed in accordance with a defined time delay and/or controlled by one or more computer components based on sensing functions of the respective touch sensor.

Figure 1:
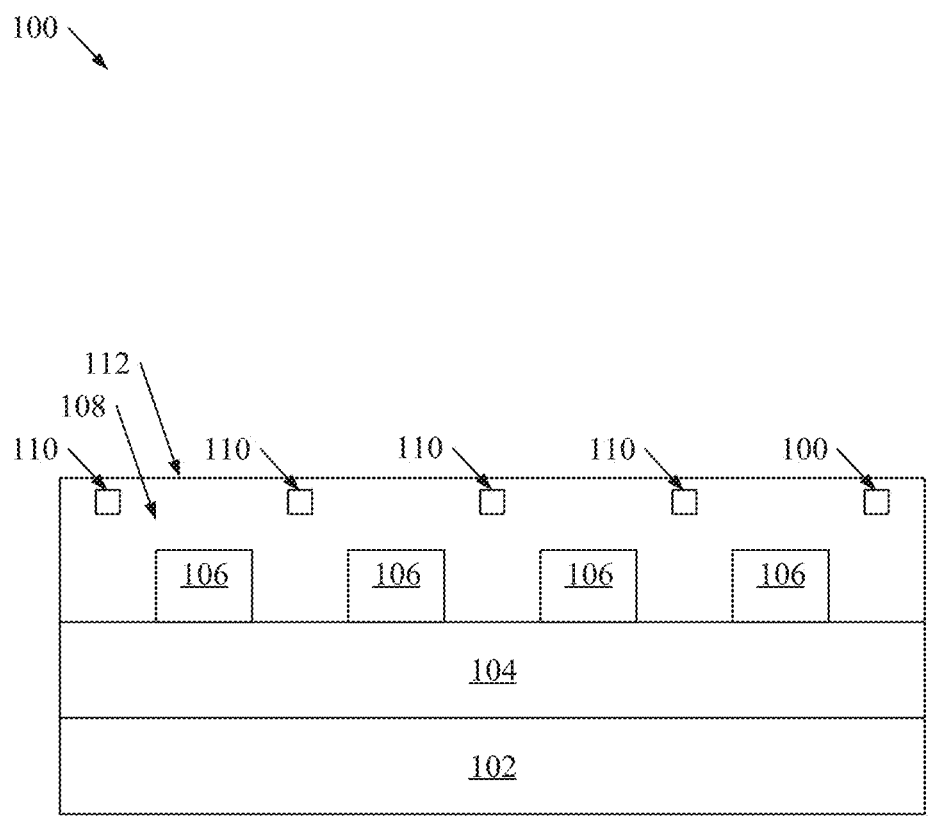
FIG. 1 illustrates a diagram of an example, non-limiting side view of a touch sensor that can perform a self-sterilization based on a detected pressure in accordance with one or more embodiments described herein.

FIG. 1 illustrates a diagram of an example, non-limiting touch sensor 100 that can perform one or more self-sterilizations based on a detected pressure in accordance with one or more embodiments described herein. The touch sensor 100 can be an apparatus that detects one or more forms of pressure. For example, the touch sensor 100 can be a biometric sensor such as a fingerprint sensor, a handprint sensor, and/or the like. Further, the touch sensor 100 can be comprised within one or more devices, such as one or more computerized devices. Example computerized devices that can comprise the touch sensor 100 can include, but are not limited to: laptop computers, desktop computers, computerized tables, smart phones, smart wearables (e.g., smart watches and/or smart bracelets), security systems, a combination thereof, and/or the like.

The touch sensor 100 can comprise one or more power sources 102, one or more sense amplifiers 104, one or more sensors 106, a protective layer 108, and/or one or more sterilization generators 110. The one or more power sources 102 can provide electricity to operate the touch sensor 100. For example, the one or more power sources 102 can comprise one or more batteries (e.g., lithium-ion batteries, lead acid batteries, and/or nickel metal hydride batteries). In another example, the one or more power sources 102 can comprise other electrical suppliers, such as solar panels. One of ordinary skill in the art will readily recognize that the type of power source 102, the number of power sources 102, and/or the dimensions of the one or more power sources 102 can vary depending on the functionality of the touch sensor 100.

As shown in FIG. 1, the one or more sensors 106 can be encapsulated by the protective layer 108. Further, the one or more sensors 106 can be operably coupled to the one or more sense amplifiers 104. In one or more embodiments, the one or more sensors 106 can be positioned adjacent to the one or more sense amplifiers 104. Further, the one or more sensors 106 can generate one or more electrical signals based on one or more pressures applied to the protective layer 108.

In one or more embodiments, the one or more sensors 106 can comprise one or more pressure sensors that can detect one or more forces being applied against the protective layer 108. For example, the one or more sensors 106 can comprise one or more capacitor plates, wherein pressure applied to the protective layer 108 can be transferred to the one or more capacitor plates to form one or more capacitors. Further, the one more capacitors, formed by the pressure applied to respective capacitor plates, can generate an electrical signal. A capacitor fingerprint sensor can be an example of a touch sensor 100 that can use one or more pressure-based sensors to detect a pressure (e.g., a touch) applied to the touch sensor 100.

Additionally, in one or more embodiments, the one or more sensors 106 can comprise one or more optical sensors that can monitor the protective layer 108 for optical variations induced by a pressure being applied to the protective layer 108 (e.g., the presence of a finger touching the protective layer 108). For example, the one or more sensors 106 can capture one or more optical images that can be analyzed by the touch sensor 100 to determine the presence and/or structural characteristics of an object touching the touch sensor 100. For instance, when an object is pressed against the protective layer 108, the one or more sensors 106 can capture one or more images of the object. The one or more images can depict, for example, light and/or dark areas of the object, which can indicate one or more unique characteristics on the surface of the object and/or whether the object is touching (e.g., thereby applying a force) the touch sensor 100. An optical fingerprint sensor can be an example of a touch sensor 100 that can use one or more optical-based sensors to detect a pressure (e.g., a touch) applied to the touch sensor 100.

Further, the one or more touch sensors 100 can comprise additional features to facilitate operation of the one or more sensors 106. For example, the one or more touch sensors 100 can additionally comprise: one or more light emitting diodes ("LEDs"), one or more prisms, one or more lenses, one or more wires, a combination thereof, and/or the like. In one or more embodiments, the one or more additional features can also be embedded, surrounded by, and/or adjacent to the protective layer 108.

The one or more sensors 106 can send one or more electrical signals to the one or more sense amplifiers 104 based on one or more detections made by the sensors 106. The one or more electrical signals can facilitate the sense amplifier 104 in determining: whether an object is touching the touch sensor 100 (e.g., whether a pressure is being applied to the touch sensor 100), one or more characteristics regarding an object touching the touch sensor 100 (e.g., uniqueness of the valleys and/or ridges in a person's finger that is touching the touch sensor 100), how much pressure is being applied to the touch sensor 100, how long pressure is being applied to the touch sensor 100, a combination thereof, and/or the like.

The one or more sense amplifiers 104 can comprise one or more integrated circuits and/or one or more computer components to facilitate generating determinations based on the electrical signals provided by the one or more sensors 106. For example, the one or more sense amplifiers 104 can comprise one or more processors. Also, in one or more embodiments, the one or more sense amplifiers 104 can be operably coupled to one or more networks that can facilitate analysis of the one or more electrical signals provided by the one or more sensors 106. The one or more networks can comprise wired and wireless networks, including, but not limited to, a cellular network, a wide area network (WAN) (e.g., the Internet) or a local area network (LAN). The one or more networks can comprise wired or wireless technology including for example, but not limited to: cellular, WAN, wireless fidelity (Wi-Fi), Wi-Max, WLAN, Bluetooth technology, a combination thereof, and/or the like.

The protective layer 108 can protect and/or insulate the one or more sensors 106. In one or more embodiments, the protective layer 108 can be an electrical insulator and a thermal conductor. Example materials that can comprise the protective layer 108 can include, but are not limited to: amorphous diamond, boron nitride, aluminum nitride, aluminum oxide, beryllium oxide, boron arsenide, a combination thereof, and/or the like. Additionally, a transparency of the protective layer 108 can varying depending on the functionality of the touch sensor 100. For example, a touch sensor 100 that comprises one or more optically-based sensors 106 can also comprise a transparent or translucent protective layer 108. In one or more embodiments, the protective layer 108 can be adjacent to the one or more sensors 106 and/or the one or more sense amplifiers 104.

Further, the protective layer 108 can encapsulate the one or more sensors 106. One of ordinary skill in the art will recognize that a thickness of the protective layer 108 can vary depending on the functionality of the touch sensor 100. For example, the protective layer 108 can have an exemplary thickness greater than or equal to 50 nanometers and less than or equal to 5 micrometers.

The one or more sterilization generators 110 can sterilize one or more surfaces of the touch sensor 100 based on a pressure (e.g., a touch) detected by the one or more sensors 106. For example, the one or more sterilization generators 110 can sterilize a surface 112 of the protective layer 108. For instance, the surface 112 can be a side of the protective layer 108 that is monitored by the one or more sensors 106 and/or can be subject to a touch (e.g., pressure).

The one or more sterilization generators 110 can perform one or more sterilizations based on one or more determinations generated by the one or more sense amplifiers 104 (e.g., which in turn can be based on one or more detections made by the one or more sensors 106). The sterilization performed by the one or more sterilization generators 110 can: eliminate one or more microbes from the protective layer 108 (e.g., from the surface 112), inhibit growth of one or more microbes on the protective layer 108 (e.g., on the surface 112), remove one or more microbes from the protective layer 108 (e.g., from the surface 112), a combination thereof, and/or the like. Further, one more or more microbes subject to sterilization by the one or more sterilization generators 110 can include, but are not limited to: Gram-positive bacteria, Gram-negative bacteria, viruses, germs, a combination thereof, and/or the like.

In one or more embodiments, the one or more sterilization generators 110 can heat the surface 112 of the protective layer 108 to facilitate sterilization. For example, the one or more sterilization generators 110 can heat the protective layer 108 (e.g., the surface 112) to an exemplary temperate greater than or equal to 140 degrees Fahrenheit (° F.) and less than or equal to 180° F. In one or more embodiments, the one or more sterilization generators 110 can heat the protective layer 108 to a temperature that can facilitate sterilization while also being safe for a human to touch. For instance, the one or more sterilization generators 110 can comprise one or more heating elements, which can include but are not limited to: resistors, metallic heating elements (e.g., nickel, chromium, an alloy thereof, and/or the like), ceramic heating elements (e.g., molybdenum disilicide, and/or the like), polymer positive temperature coefficient ("PTC") materials, a combination thereof, and/or the like. Additionally, the one or more heating elements can be heated using electrical current, which can be supplied by the one or more power sources 102. Further, a thermal conductivity of the protective layer 108 can facilitate distribution of the heat generated by the one or more sterilization generators 110 across the surface 112 to perform the sterilization.

In one or more embodiments, the one or more sterilization generators 110 can generate one or more electrical fields to facilitate sterilization of the protective layer 108. For instance, the one or more sterilization generators 110 can modify and/or otherwise manipulate a sticky coefficient of one or more microbes via one or more electric fields. Example devices that can comprise the one or more sterilization generators 110 and/or generate one or more electric fields to facilitate sterilization can include, but are not limited to, one or more electrically conductive wires. For example, the one or more sterilization generators 110 can comprise one or more conductive wires connected to the one or more power sources 102 (e.g., an electric voltage). When an object and/or individual touches the touch sensor 100, an electric pulse with an electric field (e.g., in the order of 10 kilovolts per centimeter wherein the electric voltage is one volt and the protective layer 108 is 1 micron thick) can be formed between the conductive wires and the object and/or individual. The generated electric field can sterilize (e.g., terminate) one or more microbes (e.g., germs).

In one or more embodiments, the one or more sterilization generators 110 can generate one or more magnetic fields to facilitate sterilization of the protective layer 108. For instance, the one or more sterilization generators 110 can interact with an electrical charge of the one or more microbes to facilitate sterilization. For example, the one or more sterilization components 110 can generate one or more magnetic fields to interact with and/or otherwise manipulate the polarity of one or more microbes located on the protective layer 108. In one or more embodiments, the one or more sterilization generators 110 can generate one or more magnetic fields to repel one or more microbes away from the surface 112 of the protective layer 108. In one or more embodiments, the one or more sterilization generators 110 can generate one or more magnetic fields to pull portions of the one or more microbes away from each other (e.g., thereby damaging a structural integrity of the one or more microbes). Example devices that can comprise the one or more sterilization components 110 and/or generate one or more magnetic fields to facilitate sterilization can include, but are not limited to: solenoid coils, and/or the like.

In one or more embodiments, the one or more sterilization generators 110 can perform one or more sterilization processes based on a detection by the one or more sensors 106. For example, the one or more sterilization generators 110 can perform one or more sterilization processes based on a pressure applied to the protective layer 108. Further, in one or more embodiments, the one or more sterilization generators 110 can perform one or more sterilization processes based on one or more determinations made by the one or more sense amplifiers 104. For example, the one or more sterilization generators 110 can perform one or more sterilization processes in response to one or more operations of the touch sensor 100 being completed.

While FIG. 1 depicts a touch sensor 100 comprising four sensors 106, the architecture of the touch sensor 100 is not so limited. For example, one or more touch sensors 100 described herein can comprise few or greater than the four sensors 106 depicted in FIG. 1. For instance, the touch sensor 100 can comprise greater than or equal to one sensor 106 and/or less than or equal to one million sensors 106. Further, the size of the one or more sensors 106 can vary depending on the functionality of the touch sensor 100 and/or the size of the touch sensor 100. Similarly, although FIG. 1 depicts a touch sensor 100 comprising five sterilization generators 110, the architecture of the touch sensor 100 is not so limited. For example, one or more touch sensors 100 described herein can comprise few or greater than the five sterilization generators 110 depicted in FIG. 1. For instance, the touch sensor 100 can comprise greater than or equal to one sterilization generator 110 and/or less than or equal to one hundred sterilization generators 110.

Figure 2:
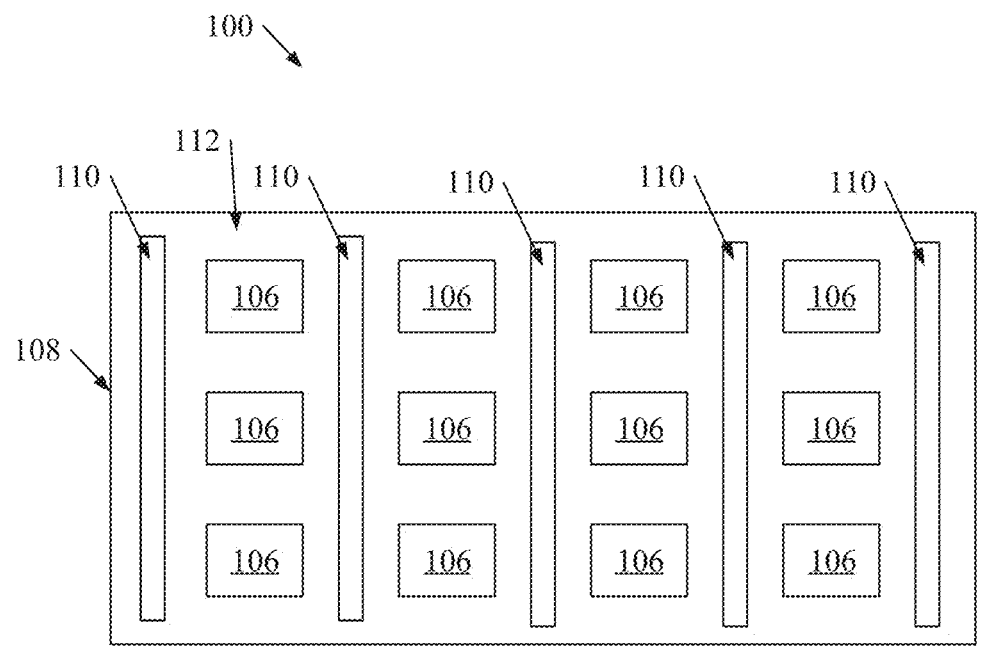
FIG. 2 illustrates a diagram of an example, non-limiting top view of a touch sensor that can perform a self-sterilization based on a detected pressure in accordance with one or more embodiments described herein.

FIG. 2 illustrates a diagram of an example, non-limiting top view of the one or more touch sensors 100 having one or more sterilization capacities in accordance with one or more embodiments described herein. Repetitive description of like elements employed in other embodiments described herein is omitted for sake of brevity.

As shown in FIG. 2, the one or more sensors 106 can be arranged in a grid and/or pattern formation. While FIG. 2 depicts a grid formation of four columns having three sensors 106, the architecture of the touch sensor 100 is not so limited. For example, the touch sensor 100 can comprise a grid and/or pattern of sensors 106 arrange in various configurations (e.g., including fewer or greater columns and/or fewer or greater rows). Further, as shown in FIG. 2, in one or more embodiments the one or more sterilization generators 110 and/or the one or more sensors 106 can be positioned evenly throughout the touch sensor 100. Additionally, in one or more embodiments, the one or more sterilization generators 110 and/or the one or more sensors 106 can be positioned with a higher density at particular locations within the touch sensor 100 as compared to other locations within the touch sensor 100 (e.g., more sterilization generators 110 positioned near the center of the touch sensor 100 than the perimeter of the touch sensor 100).

Figure 3:
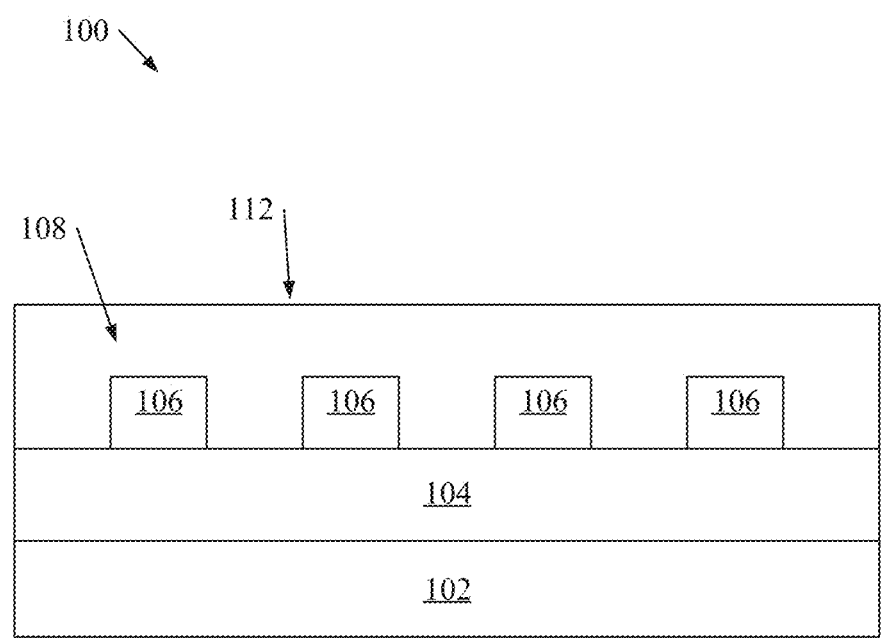
FIG. 3 illustrates a diagram of an example, non-limiting side view of a touch sensor that can perform a self-sterilization based on a detected pressure in accordance with one or more embodiments described herein.

FIG. 3 illustrates a diagram of the example, non-limiting touch sensor 100 with one or more sterilization capacities in accordance with one or more embodiments described herein. Repetitive description of like elements employed in other embodiments described herein is omitted for sake of brevity. As shown in FIG. 3, the one or more touch sensors 100 can lack separate and distinct sterilization generators 110; rather, the one or more sensors 106 can further serve to facilitate sterilization of the protective layer 108. For example, in addition to detecting pressure via various means (e.g., mechanical means and/or optical means), the one or more sensors 106 can further generate heat, electric fields, and/or magnetic fields to facilitate sterilization in accordance with the description provided herein with regards to the sterilization generators 110.

For example, the one or more sensors 106 can comprise capacitor plates, wherein activation of the capacitor plates can generate heat. Further, the protective layer 108 can conduct the heat generated by the one or more activated capacitor plates to the surface 112 of the touch sensor 100; thereby, facilitating one or more sterilization processes. For instance, the conducted heat can serve to eliminate and/or inhibit the presence of one or more microbes on the surface 112 of the protective layer 108.

Figure 4:
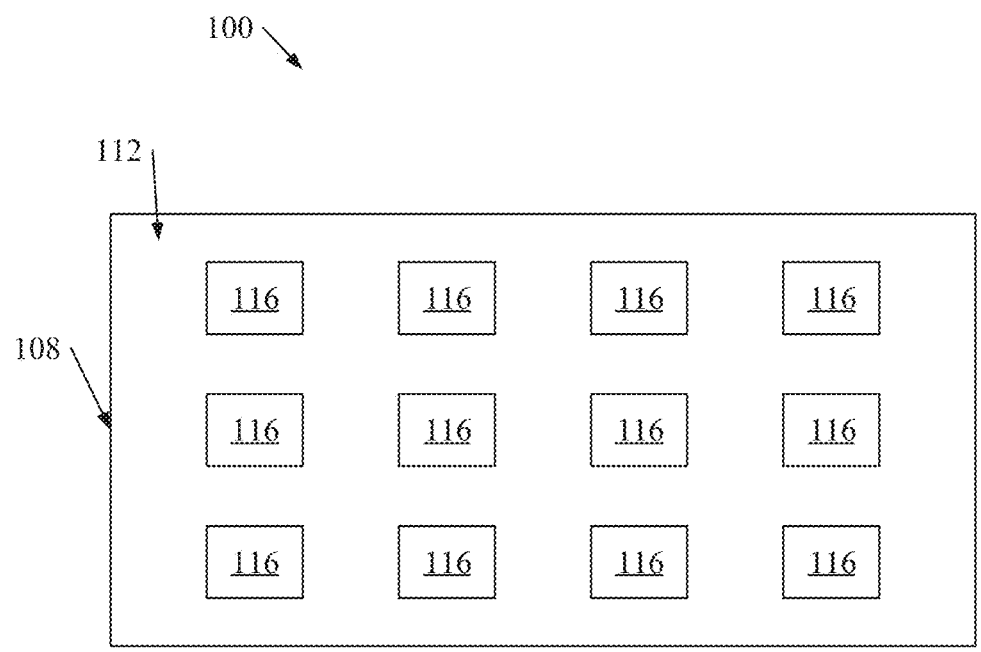
FIG. 4 illustrates a diagram of an example, non-limiting top view of a touch sensor that can perform a self-sterilization based on a detected pressure in accordance with one or more embodiments described herein.

FIG. 4 illustrates a diagram of an example, non-limiting top view of the one or more touch sensors 100 with one or more sterilization capacities in accordance with one or more embodiments described herein. Repetitive description of like elements employed in other embodiments described herein is omitted for sake of brevity. FIG. 4 can depict one or more embodiments of the touch sensor 100 in which the one or more sensors 106 can generate heat, electric fields, and/or magnetic fields to facilitate sterilization of the protective layer 108. As shown in FIG. 4, the touch sensor 100 can lack one or more distinct and/or separate sterilization generators 110, and rather utilized the one or more sensors 106 to further perform the various sterilization features described herein.

Figure 5A:
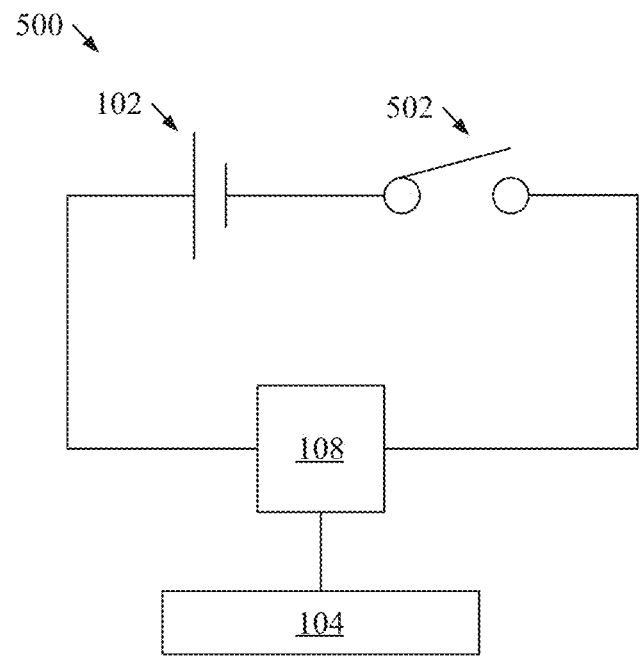
FIG. 5A illustrates a diagram of an example, non-limiting control circuitry that can be comprised within one or more touch sensors, which can perform a self-sterilization based on a detected pressure in accordance with one or more embodiments described herein.

FIG. 5A illustrates a diagram of an example, non-limiting control circuitry 500 that can facilitate controlling one or more self-sterilization processes that can be performed by one or more touch sensors 100 in accordance with one or more embodiments described herein. Repetitive description of like elements employed in other embodiments described herein is omitted for sake of brevity.

In one or more embodiments, the one or more touch sensors 100 can comprise the control circuitry 500 depicted in in FIG. 5A to facilitate controlling of one or more self-sterilization processes of the touch sensor 100. For example, the control circuitry 500 can operably couple one or more features of the touch sensor 100. For instance, as shown in FIG. 5A, the control circuitry 500 can operably couple the one or more power sources 102, the one or more sense amplifiers 104, and/or the one or more sterilization generators 110. Further, the control circuitry 500 can comprise one or more switches 502 that can be triggered by one or more delay circuits. Thus, the control circuitry 500 can facilitate activating the one or more sterilization generators 110 (e.g., based on one or more determinations of the one or more sense amplifiers 104) at a time delay to ensure that the one or more sterilization processes start at a defined period of time after the detections made by the one or more sensors 106 and/or the determinations made by the one or more sense amplifiers 104.

For example, wherein the one or more sterilization generators 110 comprise one or more heating elements, the control circuitry 500 can ensure that heat is generated at a defined time interval starting from: a time at which pressure is detected by the one or more sensors 106, and/or a time at which a determination is made by the one or more sense amplifiers 104. For instance, the one or more sterilization generators 110 can delay initialization of one or more sterilization processes (e.g., heating, generating electric fields, and/or generating magnetic fields) in accordance with a defined time interval. For example, the defined time interval that can delineate the delay can be greater than or equal to a half second and less than or equal to ten seconds (e.g., five seconds). By delaying initialization of the one or more sterilization processes (e.g., heating, generating electric fields, and/or generating magnetic fields) the touch sensor 100 (e.g., via the control circuitry 500) can ensure that the sterilization processes are not performed at an undesirable time (e.g., while one or more sensing functions of the touch sensor 100 are being performed).

Figure 5B:
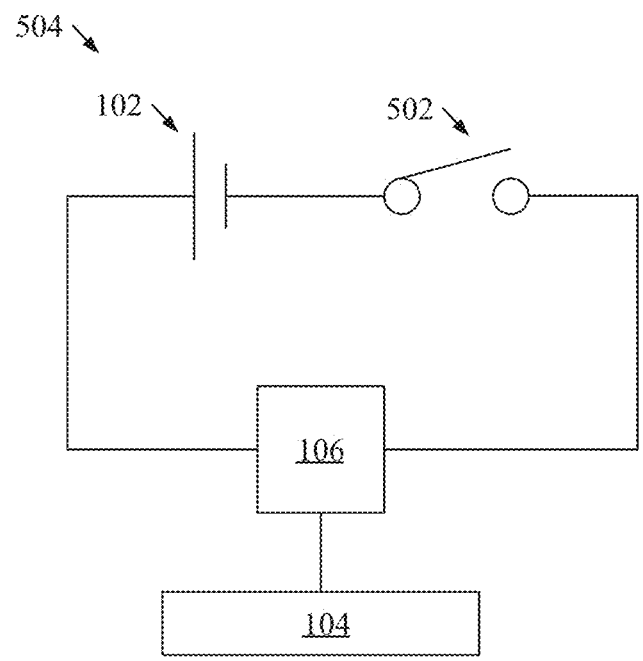
FIG. 5B illustrates a diagram of an example, non-limiting control circuitry that can be comprised within one or more touch sensors, which can perform a self-sterilization based on a detected pressure in accordance with one or more embodiments described herein.

FIG. 5B illustrates a diagram of an example, non-limiting control circuitry 504 that can facilitate controlling one or more self-sterilization processes that can be performed by one or more touch sensors 100 in accordance with one or more embodiments described herein. Repetitive description of like elements employed in other embodiments described herein is omitted for sake of brevity. The control circuitry 504 can facilitate a delayed initialization of the one or more sterilization processes as described herein with regards to the control circuitry 500, but in accordance with one or more embodiments in which the one or more sensors 106 initialize the sterilization processes rather than sterilization generators 110. For example, the control circuitry 504 can operably couple the one or more power sources 102, the one or more sense amplifiers 104, and/or the one or more sensors 106.

Figure 6A:
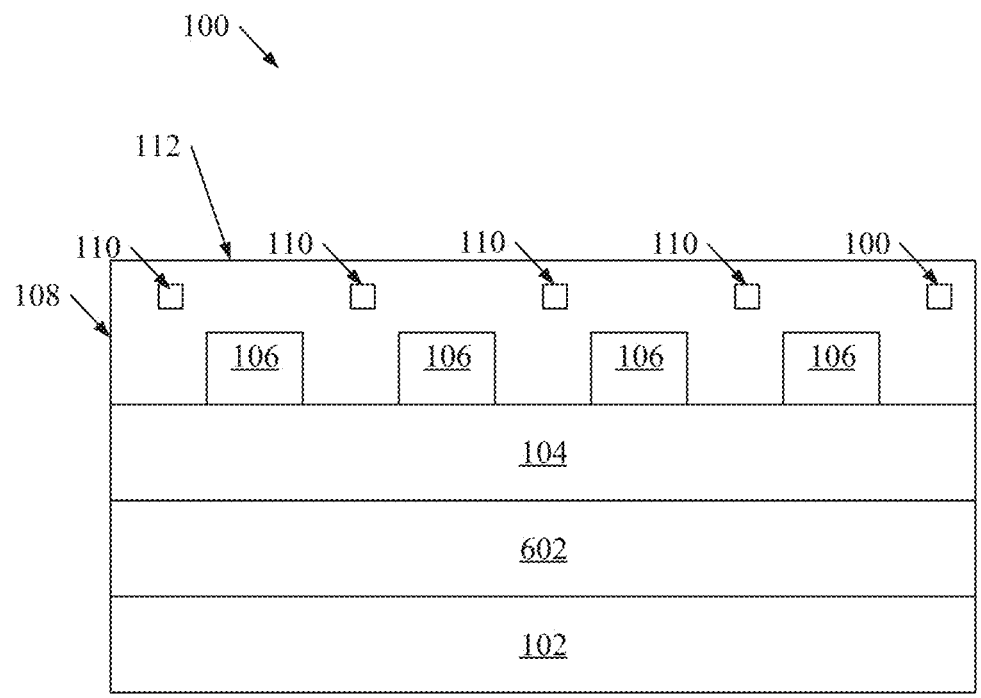
FIG. 6A illustrates a diagram of an example, non-limiting side view of a touch sensor that can perform a self-sterilization based on a detected pressure in accordance with one or more embodiments described herein.

FIG. 6A illustrates a diagram of the example, non-limiting touch sensor 100 that can further comprise one or more algorithmic controllers 602 in accordance with one or more embodiments described herein. Repetitive description of like elements employed in other embodiments described herein is omitted for sake of brevity. In one or more embodiments, the touch sensor 100 can comprise one or more algorithmic controllers 602 to facilitate control of the one or more sterilization processes. For example, the one or more algorithmic controllers 602 can facilitate initialization of the one or more sterilization processes rather that the control circuitry 500, 504 depicted in FIGS. 5A and/or 5B.

The one or more algorithmic controllers 602 can comprise one or more computer components (e.g., one or more processors), which can facilitate the application of one or more algorithms and/or programs. Further to implementing an initialization delay to the one or more sterilization processes, the one or more algorithmic controllers 602 can control one or more additional parameters and/or conditions of the one or more sterilization processes. For example, the one or more algorithmic controllers 602 can control the one or more sterilization generators 110 based on a frequency of touches (e.g., pressures) detected by the one or more sensors 106 and/or sense amplifiers 104. For instance, the one or more algorithmic controllers 602 can initiate the one or more sterilization processes based on a number of sensing functions performed by the touch sensor 100 being equal to or exceeding a predefined threshold. In another example, the one or more algorithmic controllers 602 can control the one or more sterilization generators 110 based on a severity of pressure detected by the one or more sensors 106. For instance, the one or more algorithmic controllers 602 can initiate the one or more sterilization processes based on an amount of force applied to the protective layer 108 (e.g., as determined by mechanical and/or optical means) being equal to or exceeding a predefined threshold. Other exemplary parameters and/or conditions based upon which the one or more algorithmic controllers 602 can control the one or more sterilization processes can include initiating the one or more sterilization processes at a defined time and/or during a period of inactivity of the one or more touch sensors 100. For example, the one or more algorithmic controllers 602 can be set by a user of the one or more touch sensors 100 to initiate the one or more sterilization processes in accordance with a defined schedule. In another example, the one or more algorithmic controllers 602 can analyze historic use of the one or more touch sensors 100 to determine a period of time (e.g., midnight) at which the one or more touch sensors 100 are not normally used and perform the one or more sterilization processes during such time of low activity.

While FIG. 6A depicts the one or more algorithmic controllers 602 positioned between the one or more power sources 102 and/or the one or more sense amplifiers 104, the architecture of the one or more touch sensors 100 is not so limited. For example, the one or more algorithmic controllers 602 can be positioned in a different structure within the touch sensor 100 than the structure depicted in FIG. 6A. For instance, the one or more algorithmic controllers 602 can be positioned adjacent to the protective layer 108 and/or the one or more sensors 106.

Figure 6B:
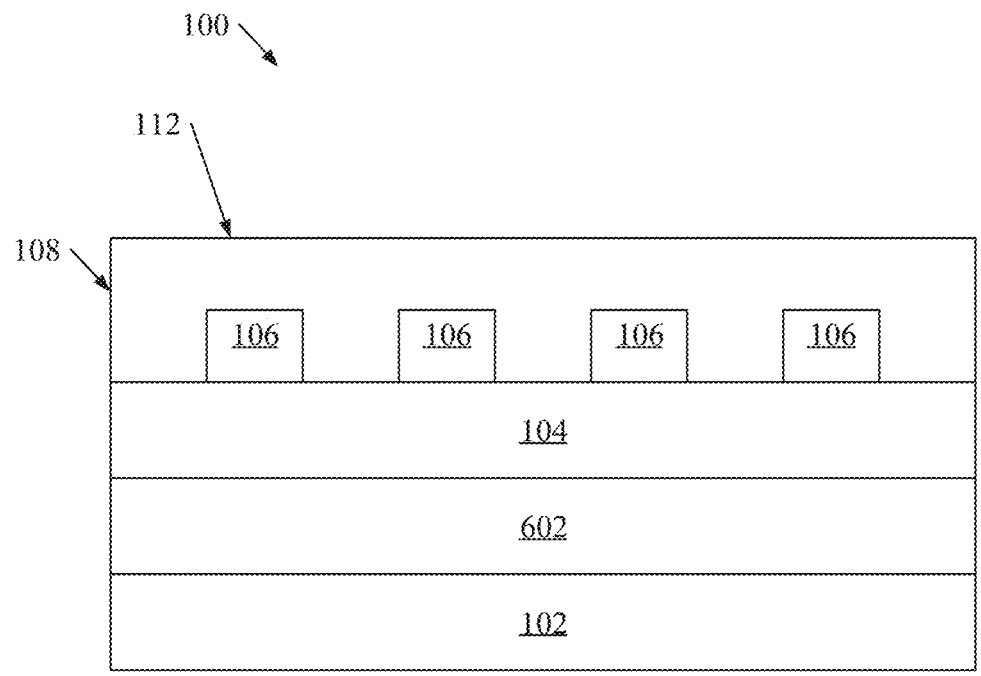
FIG. 6B illustrates a diagram of an example, non-limiting side view of a touch sensor that can perform a self-sterilization based on a detected pressure in accordance with one or more embodiments described herein.

FIG. 6B illustrates a diagram of the example, non-limiting touch sensor 100 that can further comprise one or more algorithmic controllers 602 in accordance with one or more embodiments described herein. Repetitive description of like elements employed in other embodiments described herein is omitted for sake of brevity. As shown in FIG. 6B, the one or more algorithmic controllers 602 can control the one or more sterilization processes as described herein with regards to FIG. 6A, but in accordance with one or more embodiments in which the one or more sensors 106 initialize the sterilization processes rather than sterilization generators 110. For example, the one or more algorithmic controllers 602 can control and/or otherwise influence the one or more sensors 106 to initiate and/or control the one or more sterilization processes. For instance, the one or more algorithmic controllers 602 can control the flow of electric current to the one or more sensors 106 to control heat generation, electrical field generation, and/or magnetic field generation.

Figure 7A:
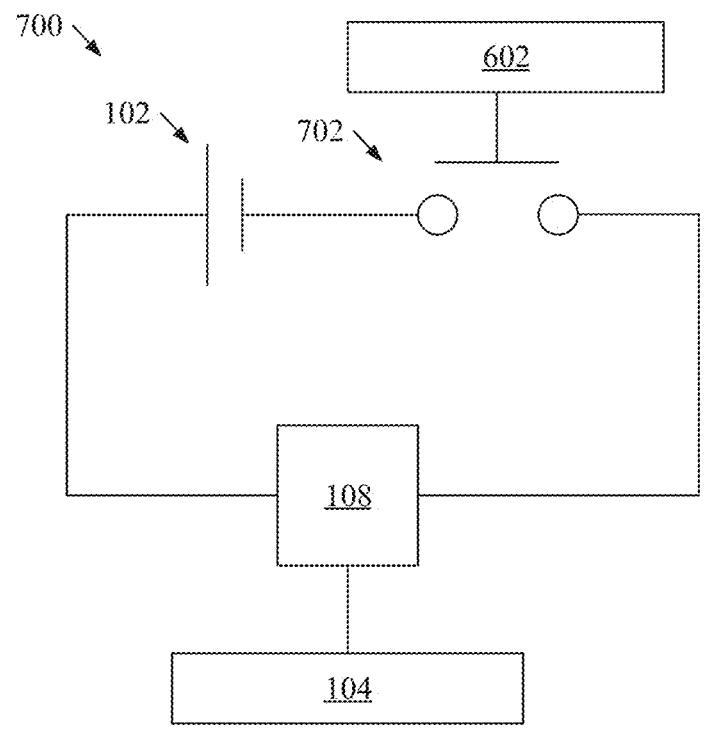
FIG. 7A illustrates a diagram of an example, non-limiting circuitry layout that can be comprised within one or more touch sensors, which can perform a self-sterilization based on a detected pressure in accordance with one or more embodiments described herein.

FIG. 7A illustrates a diagram of an example, non-limiting circuitry layout 700 that can facilitate operation of one or more self-sterilization processes performed by one or more touch sensors 100 in accordance with one or more embodiments described herein. Repetitive description of like elements employed in other embodiments described herein is omitted for sake of brevity.

In one or more embodiments, the one or more touch sensors 100 can comprise the circuitry layout 700 depicted in FIG. 7A to facilitate controlling of one or more self-sterilization processes of the touch sensor 100. For example, the circuitry layout 700 can operably couple one or more features of the touch sensor 100. For instance, as shown in FIG. 7A, the circuitry layout 700 can operably couple the one or more power sources 102, the one or more sense amplifiers 104, the one or more sterilization generators 110, and/or the one or more algorithmic controllers 602. Further, the circuitry layout 700 can comprise one or more gates 702 that can be operated by the one or more algorithmic controllers 602. Thus, the circuitry layout 700 can facilitate activating the one or more sterilization generators 110 (e.g., based on one or more determinations of the one or more sense amplifiers 104) in accordance with one or more algorithms and/or programs implemented by the one or more algorithmic controllers 602.

Figure 7B:
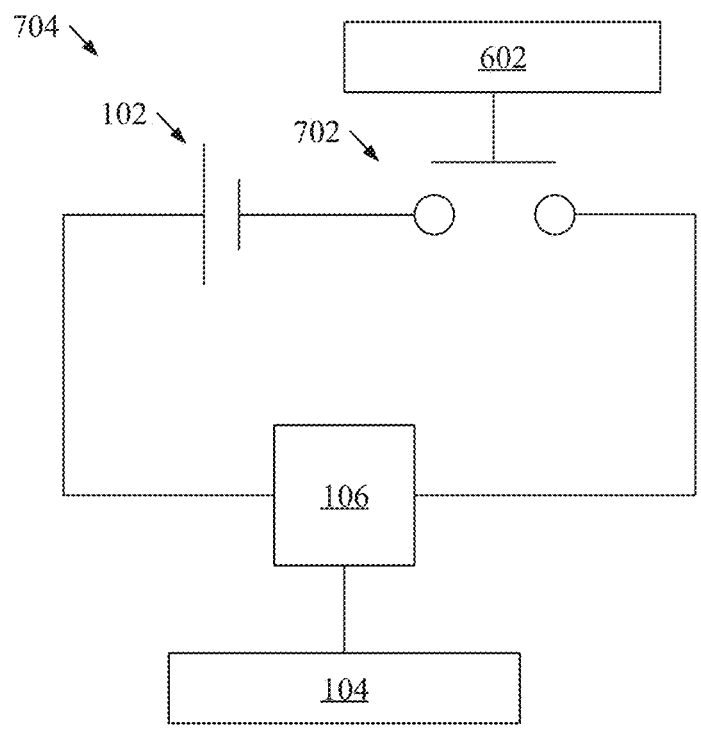
FIG. 7B illustrates a diagram of an example, non-limiting circuitry layout that can be comprised within one or more touch sensors, which can perform a self-sterilization based on a detected pressure in accordance with one or more embodiments described herein.

FIG. 7B illustrates a diagram of an example, non-limiting circuitry layout 704 that can facilitate operation of one or more self-sterilization processes performed by one or more touch sensors 100 in accordance with one or more embodiments described herein. Repetitive description of like elements employed in other embodiments described herein is omitted for sake of brevity. The circuitry layout 704 can facilitate control of the one or more sterilization processes by the one or more algorithmic controllers 602 as described herein with regards to the circuitry layout 700, but in accordance with one or more embodiments in which the one or more sensors 106 initialize the sterilization processes rather than sterilization generators 110. For example, the circuitry layout 704 can operably couple the one or more power sources 102, the one or more sense amplifiers 104, the one or more sensors 106, and/or the one or more algorithmic controllers 602.

Figure 8:
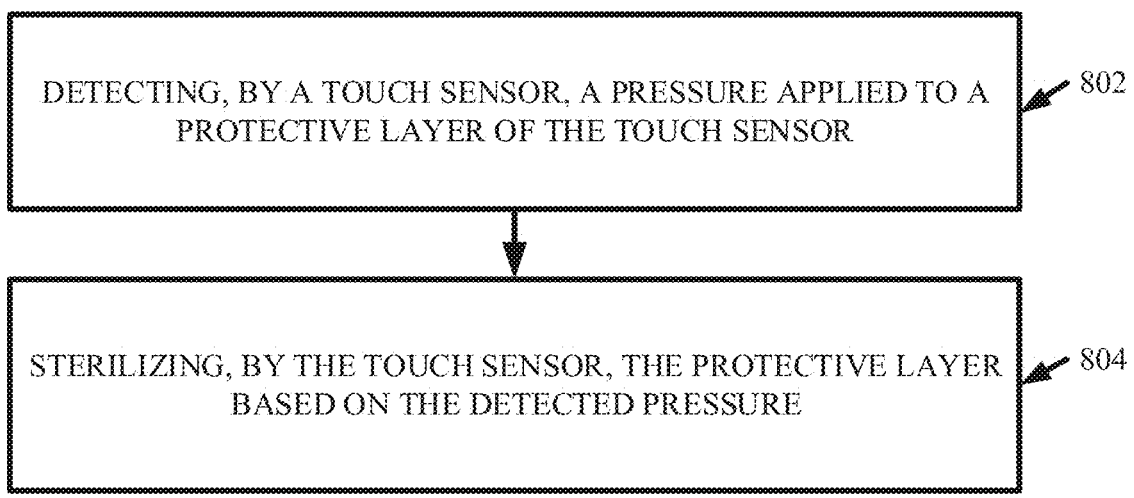
FIG. 8 illustrates a flow diagram of an example, non-limiting method that can regard an autonomous self-sterilization process, which can be performed by one or more touch sensors based on a detected pressure in accordance with one or more embodiments described herein.

FIG. 8 illustrates a flow diagram of an example, non-limiting method 800 that can facilitate one or more self-sterilizing processes by one or more touch sensors 100 in accordance with one or more embodiments described herein. Repetitive description of like elements employed in other embodiments described herein is omitted for sake of brevity.

At 802, the method 800 can comprise detecting, by a touch sensor 100, a pressure applied to a protective layer 108 of the touch sensor 100. The pressure can be detected by, for example, one or more sensors 106, which can detect the pressure by a variety of means (e.g., by mechanical means and/or by optical means). In one or more embodiments, the one or more sensors 106 can be encapsulated by the protective layer 108. Further, the pressure applied to the protective layer 108 can be caused by an object and/or an individual touching the touch sensor 100. Moreover, the touch can transport one or more microbes to a surface 112 of the protective layer 108.

At 804, the method 800 can comprise sterilizing, by the touch sensor 100, the protective layer 108 based on the detected pressure at 802. The sterilizing can be facilitated by one or more sterilization processes, which can include generating heat, generating one or more electric fields, and/or generating one or more magnetic fields in accordance with one or more embodiments described herein. For example, one or more sterilization processes can be generated by one or more sterilization generators 110 comprised within the touch sensor 100 (e.g., encapsulated by the protective layer 108) and/or by the one or more sensors 106. In one or more embodiments, the touch sensor 100 can comprise delay circuitry that can facilitate initializing the one or more sterilization processes after a defined amount of time has passed since performance and/or completion of one or more sensing functions by the touch sensor 100. Additionally, the sterilizing at 804 can comprise: eliminating one or more microbes from the protective layer 108, inhibiting growth of one or more microbes on the protective layer 108, and/or removing one or more microbes from the protective layer 108.

Figure 9:
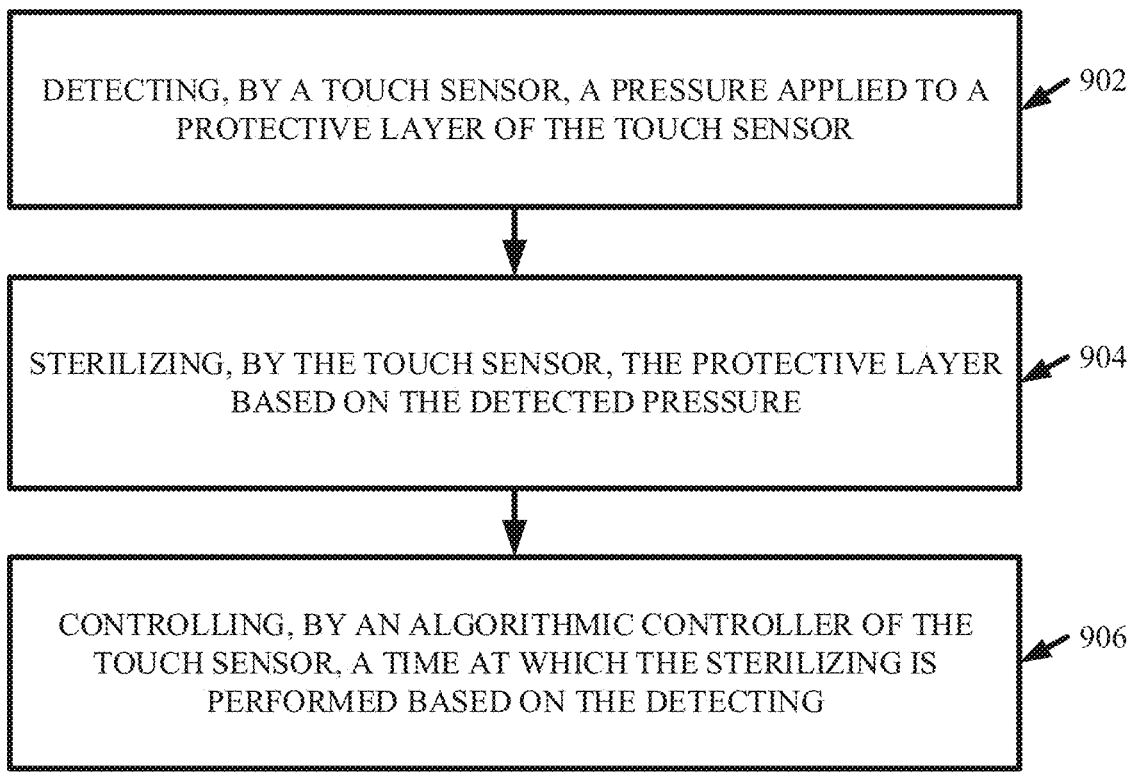
FIG. 9 illustrates a flow diagram of an example, non-limiting method that can regard an autonomous self-sterilization process, which can be performed by one or more touch sensors based on a detected pressure in accordance with one or more embodiments described herein.

FIG. 9 illustrates a flow diagram of an example, non-limiting method 900 that can facilitate one or more self-sterilizing processes by one or more touch sensors 100 in accordance with one or more embodiments described herein. Repetitive description of like elements employed in other embodiments described herein is omitted for sake of brevity.

At 902, the method 900 can comprise detecting, by a touch sensor 100, a pressure applied to a protective layer 108 of the touch sensor 100. The pressure can be detected by, for example, one or more sensors 106, which can detect the pressure by a variety of means (e.g., by mechanical means and/or by optical means). In one or more embodiments, the one or more sensors 106 can be encapsulated by the protective layer 108. Further, the pressure applied to the protective layer 108 can be caused by an object and/or an individual touching the touch sensor 100. Moreover, the touch can transport one or more microbes to a surface 112 of the protective layer 108.

At 904, the method 900 can comprise sterilizing, by the touch sensor 100, the protective layer 108 based on the detected pressure at 902. The sterilizing can be facilitated by one or more sterilization processes, which can include generating heat, generating one or more electric fields, and/or generating one or more magnetic fields in accordance with one or more embodiments described herein. For example, one or more sterilization processes can be generated by one or more sterilization generators 110 comprised within the touch sensor 100 (e.g., encapsulated by the protective layer 108) and/or by the one or more sensors 106. Additionally, the sterilizing at 804 can comprise: eliminating one or more microbes from the protective layer 108, inhibiting growth of one or more microbes on the protective layer 108, and/or removing one or more microbes from the protective layer 108.

At 906, the method 900 can further comprise controlling, by one or more algorithmic controllers 602, a time at which the sterilizing at 904 is performed based on the detecting at 902. For example, the one or more algorithmic controllers 602 can control the sterilization in accordance with one or more algorithms and/or computerized programs. For instance, the one or more algorithmic controllers 602 can control initialization of the one or more sterilization processes to be performed at a defined time interval from a time associated with: the detecting at 902, and/or one or more determinations made by the touch sensor 100 based on the detecting at 902.

Figure 10:
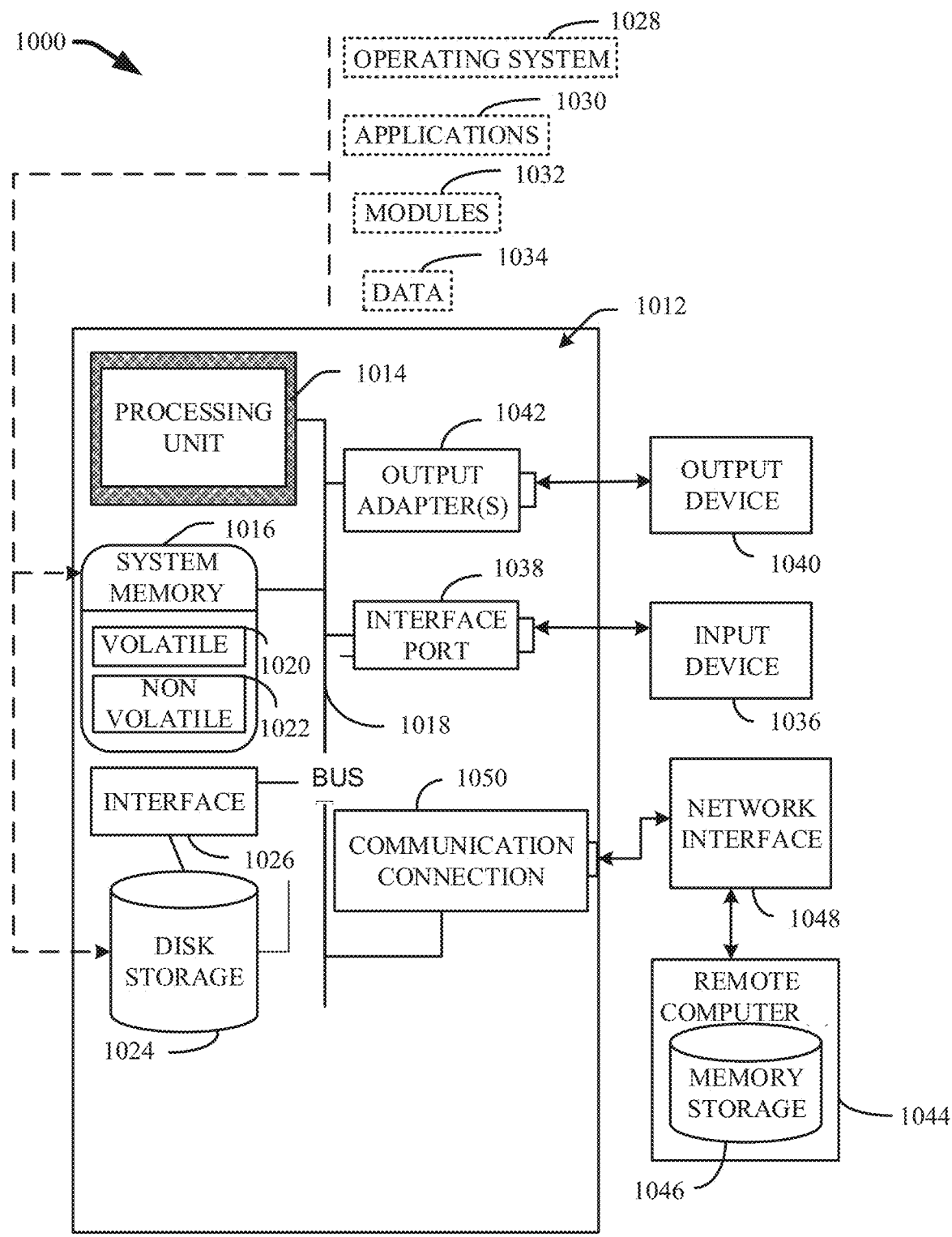
FIG. 10 illustrates a block diagram of an example, non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity. With reference to FIG. 10, a suitable operating environment 1000 for implementing various aspects of this disclosure (e.g., the one or more sense amplifiers 104 and/or the one or more algorithmic controllers 602) can include a computer 1012. The computer 1012 can also include a processing unit 1014, a system memory 1016, and a system bus 1018. The system bus 1018 can operably couple system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, can be stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface can be used, such as interface 1026. FIG. 10 also depicts software that can act as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 can take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through one or more input devices 1036. Input devices 1036 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1014 through the system bus 1018 via one or more interface ports 1038. The one or more Interface ports 1038 can include, for example, a serial port, a parallel port, a game port, and a universal serial bus (USB). One or more output devices 1040 can use some of the same type of ports as input device 1036. Thus, for example, a USB port can be used to provide input to computer 1012, and to output information from computer 1012 to an output device 1040. Output adapter 1042 can be provided to illustrate that there are some output devices 1040 like monitors, speakers, and printers, among other output devices 1040, which require special adapters. The output adapters 1042 can include, by way of illustration and not limitation, video and sound cards that provide a means of connection between the output device 1040 and the system bus 1018. It should be noted that other devices and/or systems of devices provide both input and output capabilities such as one or more remote computers 1044.

Computer 1012 can operate in a networked environment using logical connections to one or more remote computers, such as remote computer 1044. The remote computer 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer 1044. Remote computer 1044 can be logically connected to computer 1012 through a network interface 1048 and then physically connected via communication connection 1050. Further, operation can be distributed across multiple (local and remote) systems. Network interface 1048 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A touch sensor, comprising:
a heating element; and
a protective layer adjacent to the heating element, wherein the heating element, in response to the touch sensor detecting a pressure applied to the protective layer, generates heat to the protective layer after a defined period of time from the detection of the pressure, wherein the heat sterilizes the protective layer, wherein the defined period of time is selected to delay initiation of the generation of the heat for an amount of time that a fingerprint recognition operation of the touch sensor is performed, wherein the protective layer is electrically insulating and thermally conductive.

2. The touch sensor of claim 1, wherein the heating element generates the heat further in response to the pressure applied exceeding a threshold force.

3. The touch sensor of claim 1, further comprising a capacitor plate adjacent to the protective layer, and that detects the pressure.

4. The touch sensor of claim 1, wherein the heating element is a capacitor plate that detects the pressure.

5. The touch sensor of claim 1, wherein the generation of the heat only occurs in response to the touch sensor detecting the pressure applied to the protective layer, and a defined quantity of fingerprint recognition operations being performed.

6. The touch sensor of claim 1, further comprising a processor that that uses an algorithm to control a time at which the heating element generates the heat based on the pressure.

7. A device, comprising:
a touch sensor,
a heating element;
a protective layer adjacent to the heating element; and
an algorithmic controller that, in response to the touch sensor detecting a pressure applied to the protective layer, controls the heating element to generate heat to the protective layer after a defined period of time from the detection of the pressure, wherein the heat sterilizes the protective layer, wherein the defined period of time is selected to delay initiation of the generation of the heat for an amount of time that a fingerprint recognition operation of the touch sensor is performed.

8. The device of claim 7, wherein the protective layer is electrically insulating and thermally conductive.

9. The device of claim 7, wherein the algorithmic controller controls the heating element to generate the heat further in response to the pressure exceeding a threshold force.

10. The device of claim 7, wherein the touch sensor detects the pressure via a capacitor plate adjacent to the protective layer.

11. The device of claim 7, wherein the heating element is a capacitor plate that detects the pressure.

12. The device of claim 9, wherein the generation of the heat only occurs in response to the touch sensor detecting the pressure applied to the protective layer, and a defined quantity of fingerprint recognition operations being performed.

13. A touch sensor, comprising:
a heating element; and
a protective layer adjacent to the heating element, wherein the heating element, in response to the touch sensor detecting a pressure applied to the protective layer, generates heat to the protective layer after a defined period of time from the detection of the pressure, wherein the heat sterilizes the protective layer, wherein the defined period of time is selected to delay initiation of the generation of the heat for an amount of time that a fingerprint recognition operation of the touch sensor is performed, wherein the heating element generates the heat further in response to the pressure applied exceeding a threshold force.

14. The touch sensor of claim 13, further comprising a capacitor plate adjacent to the protective layer, and that detects the pressure.

15. The touch sensor of claim 13, wherein the heating element is a capacitor plate that detects the pressure.

16. The touch sensor of claim 13, wherein the generation of the heat only occurs in response to the touch sensor detecting the pressure applied to the protective layer, and a defined quantity of fingerprint recognition operations being performed.

17. The touch sensor of claim 13, further comprising a processor that that uses an algorithm to control a time at which the heating element generates the heat based on the pressure.

* * * * *